(12) United States Patent
Zhu et al.

(10) Patent No.: US 12,234,214 B2
(45) Date of Patent: Feb. 25, 2025

(54) METHOD FOR CONTINUOUSLY SYNTHESIZING 5-HYDROXYMETHYLFURFURAL BY USING MICRO-CHANNEL REACTOR

(71) Applicant: CHINA CONSTRUCTION INDUSTRIAL & ENERGY ENGINEERING GROUP CO., LTD., Nanjing (CN)

(72) Inventors: Kai Zhu, Nanjing (CN); Yiping Huang, Nanjing (CN); Meng Hu, Nanjing (CN); Changhai Yue, Nanjing (CN); Jingjing Huang, Nanjing (CN); Shuangtao Li, Nanjing (CN); Kai Guo, Nanjing (CN); Zheng Fang, Nanjing (CN)

(73) Assignee: CHINA CONSTRUCTION INDUSTRIAL & ENERGY ENGINEERING GROUP CO., LTD, Nanjing (CN)

( * ) Notice: Subject to any disclaimer, the term of this patent is extended or adjusted under 35 U.S.C. 154(b) by 0 days.

(21) Appl. No.: 18/778,902

(22) Filed: Jul. 19, 2024

(65) Prior Publication Data
US 2024/0376064 A1 Nov. 14, 2024

Related U.S. Application Data

(63) Continuation of application No. PCT/CN2022/131016, filed on Nov. 10, 2022.

(30) Foreign Application Priority Data

Sep. 30, 2022 (CN) .......................... 202211231876.8

(51) Int. Cl.
C07D 307/48 (2006.01)
B01J 19/00 (2006.01)

(52) U.S. Cl.
CPC ........ *C07D 307/48* (2013.01); *B01J 19/0013* (2013.01); *B01J 19/0093* (2013.01)

(58) Field of Classification Search
CPC .. C07D 307/48; B01J 19/0013; B01J 19/0093
(Continued)

(56) References Cited

FOREIGN PATENT DOCUMENTS

CN 102947346 A 2/2013
CN 103788034 A 5/2014
(Continued)

OTHER PUBLICATIONS

Internation Search Report of PCT/CN2022/131016, Mailed Apr. 7, 2023.
(Continued)

*Primary Examiner* — Taylor V Oh

(57) ABSTRACT

The present discloses relates to a method for continuously synthesizing 5-hydroxymethylfurfural by using a micro-channel reactor, which belongs to the technical field of micro-chemical engineering. The method includes: separately conveying an aqueous glucose solution, which contains $FeCl_3$ and HCl, and methyl butyl ketone to a T-shaped micro-mixer, the T-shaped micro-mixer being in communication with a capillary tube; then enabling an aqueous glucose solution phase and a methyl butyl ketone phase to flow in the capillary tube in a segmented flow manner while performing an HMF synthesis reaction; and collecting a reaction product flowing out of the capillary tube, wherein HMF generated by the reaction is present in an organic phase of the reaction product. The method is easy to operate, has a controllable process, high product yield, a low by-product amount and a short synthesis period, and is a green method for efficient and continuous synthesis of HMF.

5 Claims, 1 Drawing Sheet

(58) Field of Classification Search
USPC ........................................................ 549/489
See application file for complete search history.

(56) References Cited

FOREIGN PATENT DOCUMENTS

| CN | 105777674 A | | 7/2016 |
|---|---|---|---|
| CN | 114315768 A | | 4/2022 |
| CN | 114315767 A | * | 12/2022 |
| DE | 102011105758 A1 | | 12/2012 |

OTHER PUBLICATIONS

Li Guangxiao et al., "Research progress on micro-scale internal liquid-liquid mass transfer and reaction process enhancement", CIESC Journal, vol. 72, Issue 1, Sep. 22, 2020, pp. 452-467.

Ye Xin, "Continuous-Flow Process for the Synthesis of p-Cresol and Deoxyarbutin", Master's thesis, Jul. 15, 2019, Full Text.

Mu Jinxia, Yin Xuefeng, "Application of Microfluidic Reactors on Synthesis Reactions", Progress in Chemistry, vol. 20, Issue 1, Jan. 24, 2008, pp. 60-75.

* cited by examiner

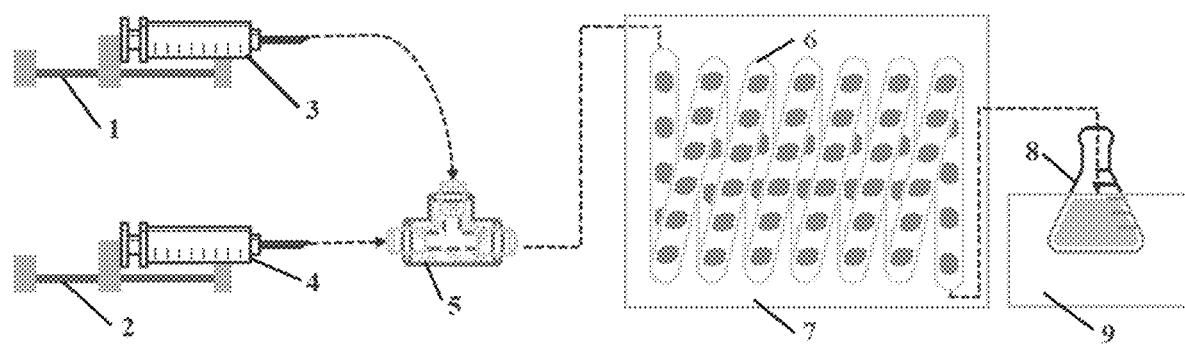

METHOD FOR CONTINUOUSLY SYNTHESIZING 5-HYDROXYMETHYLFURFURAL BY USING MICRO-CHANNEL REACTOR

CROSS-REFERENCE TO RELATED APPLICATIONS

The present disclosure is a continuation-application of International (PCT) Patent Application No. PCT/CN2022/131016, filed on Nov. 10, 2022, which claims priority of Chinese Patent Application No. 202211231876.8, filed on Sep. 30, 2022, the entire contents of which are hereby incorporated by reference in their entirety.

TECHNICAL FIELD

The present disclosure relates to a method for continuously synthesizing 5-hydroxymethylfurfural by using a micro-channel reactor, and belongs to the technical field of micro-chemical engineering.

BACKGROUND OF THE INVENTION

The massive exploitation and utilization of non-renewable fossil energy such as coal and oil have produced a large amount of harmful substances such as $CO_2$ and sulfides, resulting in a series of ecological and environmental problems such as global warming and rising sea levels, which pose severe challenges to the sustainable development of economy and society. Therefore, it is very important to develop a renewable resource with abundant production.

In recent years, the technology related to the preparation of chemicals and fuels using lignin biomass as raw materials has gradually attracted the attention of researchers. Since lignin fibers are difficult to convert directly, they can be hydrolyzed into water-soluble sugars for the synthesis of chemicals and fuels. Among them, 5-hydroxymethylfurfural (HMF) is an important platform compound that can be generated by further dehydration of glucose and fructose obtained from lignocellulose hydrolysis. Due to the presence of the aldehyde group and hydroxyl in its structure, HMF has relatively active properties and can be used as a raw material for many high value-added plastics and biofuels. For example, HMF can be converted into 2,5-furandicarboxylic acid (FDCA), 2,5-furandimethanol (FDM), and so on.

Currently, there are various biomass resources that can be converted into HMF through certain conversion pathways. Firstly, the biomass (polysaccharides) is converted into hexoses (glucose or fructose) under the action of a catalyst. Among them, glucose can be converted into fructose by isomerization, and fructose generates specific intermediates under the action of an acidic catalyst. The intermediates then undergo multiple dehydration steps to produce HMF. Glucose, a widely available hexose, is commonly used for the preparation of HMF. However, in the current technology of synthesizing HMF from glucose, the reaction process has disadvantages such as many by-products, low HMF selectivity, inability to precisely control residence time, and poor catalyst stability.

SUMMARY OF THE INVENTION

To address the problems present in the current HMF synthesis technology utilizing glucose, the present disclosure provides a method for continuously synthesizing 5-hydroxymethylfurfural by using a micro-channel reactor. Based on the micro-channel reactor, $FeCl_3$ and HCl are used as homogeneous catalysts in the aqueous phase, while methyl butyl ketone is used as the organic phase for in-situ HMF extraction. The reaction time can be significantly shortened from tens of hours in a batch reactor to less than 30 min. This method improves the selectivity of HMF, reduces the amount of by-products, achieves high yield, and features simple and controllable continuous operation.

The objective of the present disclosure is achieved by the following technical solutions.

A method for continuously synthesizing 5-hydroxymethylfurfural by using a micro-channel reactor, wherein the micro-channel reactor includes a T-shaped micro-mixer and a capillary tube. A T-shaped channel inside the T-shaped micro-mixer communicates with three ports correspondingly, one port is connected with one end of the capillary tube, and the other two ports are used as feed ports for a glucose aqueous solution and methyl butyl ketone. The other end of the capillary tube is provided with a back pressure valve to ensure that the synthesis reaction of 5-hydroxymethylfurfural is carried out under stable pressure.

The specific steps for continuously synthesizing 5-hydroxymethylfurfural are as follows:

an aqueous glucose solution containing $FeCl_3$ and HCl is formulated, the aqueous glucose solution and methyl butyl ketone are separately conveying to a T-shaped micro-mixer, then the aqueous glucose solution phase and methyl butyl ketone phase are enabled to flow in the capillary tube in a segmented flow manner while a 5-hydroxymethylfurfural synthesis reaction is performed, and a reaction product flowing out of the capillary tube is collected. The 5-hydroxymethylfurfural produced in the reaction exists in the organic phase of the reaction product. Depending on the actual needs, subsequent processing can be carried out to purify the 5-hydroxymethylfurfural from the reaction product.

Preferably, the reaction in the capillary tube is carried out at a temperature of 120~180° C. for 5~30 min (or the residence time in a heating zone of the capillary tube) under a pressure of 0.1~2 MPa. More preferably, the reaction in the capillary tube is carried out at a temperature of 150~170° C. for 12~20 min under a pressure of 0.5~1.2 MPa.

Preferably, a volume ratio of the aqueous glucose solution to methyl butyl ketone conveyed into the T-shaped micro-mixer is 1:(1~10), more preferably 1:(3~5).

Preferably, in the aqueous glucose solution, the concentration of glucose is 0.5~1.2 mol/L, the concentration of $FeCl_3$ is 10~100 mmol/L, and the concentration of HCl is 10~100 mmol/L. More preferably, a molar ratio of $FeCl_3$ to HCl in the aqueous glucose solution is (0.9~1.1):1.

Preferably, the capillary tube is placed in a thermostat bath to control the reaction temperature of the capillary tube to be stable.

Preferably, a collection temperature of the reaction product is controlled to be 5° C. or below to inhibit the reaction from proceeding. More preferably, the reaction product is collected under the ice-water bath condition, ensuring that the collection temperature is 5° C. or below.

Preferably, the inner diameter of the capillary tube is 200~1000 μm.

BENEFICIAL EFFECTS (1) The fluid channels within the micro-reactor are in the order of micrometers or sub-millimeters (typically tens to hundreds of micrometers). Due to the short transfer distances, high concentration/temperature gradients, and the enormous specific surface area of the system at the microscale, the heat and mass transfer coefficients in the micro-reactor are 1 to 3 orders of magnitude higher than those in traditional chemical equipment. Compared with the current technology of batch reactor synthesis of HMF, the present disclosure based on the micro-channel reactor for continuous synthesis of HMF can significantly reduce the reaction time to within 30 min, greatly improving the process efficiency.

(2) Glucose can be converted into fructose through isomerization. Under the action of an acidic catalyst, fructose generates specific intermediates, which then undergoes multiple dehydration steps to form HMF. However, many by-products are produced during the process of HMF generation, including soluble polymers and insoluble humins during the dehydration of the intermediates. Additionally, HMF can further produce soluble substances such as levulinic acid and formic acid in an aqueous solution. The present disclosure employs $FeCl_3$ and HCl as homogeneous catalysts in the aqueous phase, while using methyl butyl ketone as the organic phase for in-situ HMF extraction and continuous synthesis of HMF. This method can reduce the concentration of HMF generated in the aqueous phase, promote the conversion of glucose to HMF, and inhibit the occurrence of side reactions of HMF, effectively improving the selectivity of HMF.

(3) In the present disclosure, the aqueous glucose solution is used as a dispersed phase, while methyl butyl ketone serves as a continuous phase. By adjusting the volumes of the aqueous glucose solution and methyl butyl ketone conveyed into the T-shaped micro-mixer, it not only facilitates the formation of a stable segmented flow within the capillary tube, but also aids in the in-situ extraction of HMF, thereby improving the selectivity of HMF.

(4) By collecting the reaction product at a temperature of 5° C. or below, the present disclosure can inhibit the continuation of the reaction, which is beneficial for reducing by-products and improving the yield of the target product.

(5) The method described in the present disclosure is simple to operate, with controllable processes, high product yield, a low by-product amount, and a short synthesis cycle, and is a green method for efficient and continuous synthesis of HMF.

BRIEF DESCRIPTION OF DRAWINGS

FIG. 1 is a schematic diagram showing the structure of an apparatus employed for the continuous synthesis of 5-hydroxymethylfurfural in Examples.

Wherein, 1—syringe pump I, 2—syringe pump II, 3—syringe I, 4—syringe II, 5—T-shaped micro-mixer, 6—capillary tube, 7—thermostat bath, 8—collector, 9—cooling bath.

DETAILED DESCRIPTION OF THE INVENTION

The disclosure will now be further described with reference to the following specific embodiments, wherein the methods are conventional methods unless otherwise specified, and the raw materials are available from publicly available commercial channels unless otherwise specified. In addition, in the description of the present disclosure, it should be understood that the terms "up", "down", "front", "back", "left", "right", "top", "bottom", "inside", "outside" and the like indicate the orientation or positional relationship based on the orientation or positional relationship shown in the accompanying drawings, only for ease of description of the disclosure and for simplicity of description, the terms are not intended to indicate or imply that the device or element referred to must have a particular orientation, be constructed and operate in a particular orientation, and therefore should not be construed as limiting the disclosure.

In the following examples, the apparatus used for continuously synthesizing 5-hydroxymethylfurfural includes a syringe pump I 1, a syringe pump II 2, a syringe I 3, a syringe II 4, a T-shaped micro-mixer 5, a capillary tube 6, a thermostat bath 7, a collector 8, and a cooling bath 9, as shown in FIG. 1;

A T-shaped channel inside the T-shaped micro-mixer 5 communicates with three ports correspondingly, a port corresponding to one end of a vertical channel is connected with a syringe I 3, the syringe I 3 is mounted on a syringe pump I 1, an aqueous glucose solution is conveyed into the T-shaped micro-mixer 5 under the action of the syringe I 3 and the syringe pump I 1, two ports corresponding to two ends of a horizontal channel are connected one-to-one with the syringe II 4 and the capillary tube 6, respectively, the syringe II 4 is mounted on the syringe pump II 2, and the methyl butyl ketone is conveyed into the T-shaped micro-mixer 5 under the action of the syringe II 4 and the syringe pump II 2;

The capillary tube 6 is selected as a PFA capillary tube (soluble polyperfluorinated ethylene propylene tube) with an inner diameter of 600 μm. The capillary tube 6 is placed in a thermostat bath 7 to ensure that the reaction process temperature is within the range of 130 to 180° C. A back pressure valve is installed at the end of the capillary tube 6 to ensure that the HMF synthesis reaction proceeds under stable pressure.

The collector 8 is placed in a cooling bath 9 filled with ice water, keeping the collection temperature of the reaction product at 5° C. or below to inhibit the continuation of the reaction.

Example 1

(1) An aqueous glucose solution containing $FeCl_3$ and HCl was formulated, wherein concentrations of glucose, $FeCl_3$ and HCl in the aqueous glucose solution were 1 mol/L, 40 mmol/L, and 40 mmol/L, respectively; and (2) the syringe pump I 1 and syringe pump II 2 were regulated, the aqueous glucose solution and methyl butyl ketone were simultaneously conveyed into the T-shaped micro-mixer 5 at a flow rate of 1:4 by volume. Subsequently, the aqueous glucose solution phase and the methyl butyl ketone phase flowed in a segmented flow manner within the capillary tube 6, while the 5-hydroxymethylfurfural synthesis reaction was performed. The reaction was carried out at a temperature of 160° C. for 16 min (or the residence time in the heating zone of the capillary tube 6) under a pressure of 1 MPa. The reaction product flowing out from the capillary tube was collected in the collector 8 at a temperature of 5° C. or below, and the generated 5-hydroxymethylfurfural was present in the organic phase of the reaction product.

After separating the aqueous and organic phases of the collected reaction product, the yield of the target product, 5-hydroxymethylfurfural, was determined through chromatography analysis to be 93%.

Example 2

(1) An aqueous glucose solution containing $FeCl_3$ and HCl was formulated, wherein concentrations of glucose, $FeCl_3$ and HCl in the aqueous glucose solution were 1 mol/L, 20 mmol/L, and 20 mmol/L, respectively;

(2) the syringe pump I 1 and syringe pump II 2 were regulated, the aqueous glucose solution and methyl butyl ketone were simultaneously conveyed into the T-shaped micro-mixer 5 at a flow rate of 1:4 by volume. Subsequently, the aqueous glucose solution phase and the methyl butyl ketone phase flowed in a segmented flow manner within the capillary tube 6, while the 5-hydroxymethylfurfural synthesis reaction was performed. The reaction was carried out at a temperature of 160° C. for 16 min under a pressure of 1 MPa. The reaction product flowing out from the capillary tube was collected in the collector 8 at a temperature of 5° C. or below, and the generated 5-hydroxymethylfurfural was present in the organic phase of the reaction product.

After separating the aqueous and organic phases of the collected reaction product, the yield of the target product, 5-hydroxymethylfurfural, was determined through chromatography analysis to be 89%.

Example 3

(1) An aqueous glucose solution containing $FeCl_3$ and HCl was formulated, wherein concentrations of glucose, $FeCl_3$ and HCl in the aqueous glucose solution were 1 mol/L, 40 mmol/L, and 40 mmol/L, respectively;

(2) the syringe pump I 1 and syringe pump II 2 were regulated, the aqueous glucose solution and methyl butyl ketone were simultaneously conveyed into the T-shaped micro-mixer 5 at a flow rate of 1:6 by volume. Subsequently, the aqueous glucose solution phase and the methyl butyl ketone phase flowed in a segmented flow manner within the capillary tube 6, while the 5-hydroxymethylfurfural synthesis reaction was performed. The reaction was carried out at a temperature of 160° C. for 16 min under a pressure of 1 MPa. The reaction product flowing out from the capillary tube was collected in the collector 8 at a temperature of 5° C. or below, and the generated 5-hydroxymethylfurfural was present in the organic phase of the reaction product.

After separating the aqueous and organic phases of the collected reaction product, the yield of the target product, 5-hydroxymethylfurfural, was determined through chromatography analysis to be 85%.

Example 4

(1) An aqueous glucose solution containing $FeCl_3$ and HCl was formulated, wherein concentrations of glucose, $FeCl_3$ and HCl in the aqueous glucose solution were 1 mol/L, 40 mmol/L, and 40 mmol/L, respectively;

(2) the syringe pump I 1 and syringe pump II 2 were regulated, the aqueous glucose solution and methyl butyl ketone were simultaneously conveyed into the T-shaped micro-mixer 5 at a flow rate of 1:4 by volume. Subsequently, the aqueous glucose solution phase and the methyl butyl ketone phase flowed in a segmented flow manner within the capillary tube 6, while the 5-hydroxymethylfurfural synthesis reaction was performed. The reaction was carried out at a temperature of 120° C. for 16 min under a pressure of 1 MPa. The reaction product flowing out from the capillary tube was collected in the collector 8 at a temperature of 5° C. or below, and the generated 5-hydroxymethylfurfural was present in the organic phase of the reaction product.

After separating the aqueous and organic phases of the collected reaction product, the yield of the target product, 5-hydroxymethylfurfural, was determined through chromatography analysis to be 80%.

Example 5

(1) An aqueous glucose solution containing $FeCl_3$ and HCl was formulated, wherein concentrations of glucose, $FeCl_3$ and HCl in the aqueous glucose solution were 1 mol/L, 36 mmol/L, and 40 mmol/L, respectively;

(2) the syringe pump I 1 and syringe pump II 2 were regulated, the aqueous glucose solution and methyl butyl ketone were simultaneously conveyed into the T-shaped micro-mixer 5 at a flow rate of 1:4 by volume. Subsequently, the aqueous glucose solution phase and the methyl butyl ketone phase flowed in a segmented flow manner within the capillary tube 6, while the 5-hydroxymethylfurfural synthesis reaction was performed. The reaction was carried out at a temperature of 160° C. for 16 min under a pressure of 1 MPa. The reaction product flowing out from the capillary tube was collected in the collector 8 at a temperature of 5° C. or below, and the generated 5-hydroxymethylfurfural was present in the organic phase of the reaction product.

After separating the aqueous and organic phases of the collected reaction product, the yield of the target product, 5-hydroxymethylfurfural, was determined through chromatography analysis to be 91%.

Example 6

(1) An aqueous glucose solution containing $FeCl_3$ and HCl was formulated, wherein concentrations of glucose, $FeCl_3$ and HCl in the aqueous glucose solution were 1 mol/L, 40 mmol/L, and 40 mmol/L, respectively;

(2) the syringe pump I 1 and syringe pump II 2 were regulated, the aqueous glucose solution and methyl butyl ketone were simultaneously conveyed into the T-shaped micro-mixer 5 at a flow rate of 1:4 by volume. Subsequently, the aqueous glucose solution phase and the methyl butyl ketone phase flowed in a segmented flow manner within the capillary tube 6, while the 5-hydroxymethylfurfural synthesis reaction was performed. The reaction was carried out at a temperature of 160° C. for 8 min under a pressure of 1 MPa. The reaction product flowing out from the capillary tube was collected in the collector 8 at a temperature of 5°

C. or below, and the generated 5-hydroxymethylfurfural was present in the organic phase of the reaction product.

After separating the aqueous and organic phases of the collected reaction product, the yield of the target product, 5-hydroxymethylfurfural, was determined through chromatography analysis to be 82%.

Example 7

(1) An aqueous glucose solution containing $FeCl_3$ and HCl was formulated, wherein concentrations of glucose, $FeCl_3$ and HCl in the aqueous glucose solution were 1 mol/L, 40 mmol/L, and 40 mmol/L, respectively;

(2) the syringe pump I 1 and syringe pump II 2 were regulated, the aqueous glucose solution and methyl butyl ketone were simultaneously conveyed into the T-shaped micro-mixer 5 at a flow rate of 1:4 by volume. Subsequently, the aqueous glucose solution phase and the methyl butyl ketone phase flowed in a segmented flow manner within the capillary tube 6, while the 5-hydroxymethylfurfural synthesis reaction was performed. The reaction was carried out at a temperature of 160° C. for 16 min under a pressure of 0.6 MPa. The reaction product flowing out from the capillary tube was collected in the collector 8 at a temperature of 5° C. or below, and the generated 5-hydroxymethylfurfural was present in the organic phase of the reaction product.

After separating the aqueous and organic phases of the collected reaction product, the yield of the target product, 5-hydroxymethylfurfural, was determined through chromatography analysis to be 87%.

In view of the above, the above is only the preferred examples of the present disclosure, and is not intended to limit the scope of protection of the present disclosure. All such modifications, equivalents, improvements, and the like, should be included within the and scope of protection of the present disclosure.

The invention claimed is:

1. A method for continuously synthesizing 5-hydroxymethylfurfural by using a micro-channel reactor, wherein the micro-channel reactor comprises a T-shaped micro-mixer and a capillary tube, a T-shaped channel inside the T-shaped micro-mixer communicates with three ports correspondingly, a port corresponding to one end of a vertical channel is connected with a syringe I, the syringe I is mounted on a syringe pump I, an aqueous glucose solution is conveyed into the T-shaped micro-mixer under an action of the syringe I and the syringe pump I, two ports corresponding to two ends of a horizontal channel are connected one-to-one with a syringe II and the capillary tube, respectively, the syringe II is mounted on a syringe pump II, and methyl butyl ketone is conveyed into the T-shaped micro-mixer under an action of the syringe II and the syringe pump II; another end of the capillary tube is provided with a back pressure valve;

wherein, specific steps for continuously synthesizing 5-hydroxymethylfurfural are as follows:

formulating an aqueous glucose solution containing $FeCl_3$ and HCl, separately conveying the aqueous glucose solution and methyl butyl ketone to a T-shaped micro-mixer, then enabling a aqueous glucose solution phase and a methyl butyl ketone phase to flow in the capillary tube in a segmented flow manner while performing a 5-hydroxymethylfurfural synthesis reaction, and collecting a reaction product flowing out of the capillary tube, wherein 5-hydroxymethylfurfural generated by the reaction is present in an organic phase of the reaction product;

wherein, a volume ratio of the aqueous glucose solution to methyl butyl ketone conveyed into the T-shaped micro-mixer is 1:(3~5); an inner diameter of the capillary tube is 200~1000 μm;

wherein the 5-hydroxymethylfurfural synthesis reaction in the capillary tube is carried out at a temperature of 150~170° C. for 12~20 min under a pressure of 0.5~1.2 MPa.

2. The method for continuously synthesizing 5-hydroxymethylfurfural by using a micro-channel reactor according to claim 1, wherein the 5-hydroxymethylfurfural synthesis reaction in the capillary tube is carried out at a temperature of 120~180° C. for 5~30 min under a pressure of 0.1~2 MPa.

3. The method for continuously synthesizing 5-hydroxymethylfurfural by using a micro-channel reactor according to claim 1, wherein in the aqueous glucose solution, a concentration of glucose is 0.5~1.2 mol/L, a concentration of $FeCl_3$ is 10~100 mmol/L, and the concentration of HCl is 10~100 mmol/L.

4. The method for continuously synthesizing 5-hydroxymethylfurfural by using a micro-channel reactor according to claim 3, wherein a molar ratio of $FeCl_3$ to HCl in the aqueous glucose solution is (0.9~1.1):1.

5. The method for continuously synthesizing 5-hydroxymethylfurfural by using a micro-channel reactor according to claim 1, wherein a collection temperature of the reaction product is controlled to be 5° C. or below.

* * * * *